Figure 1A:
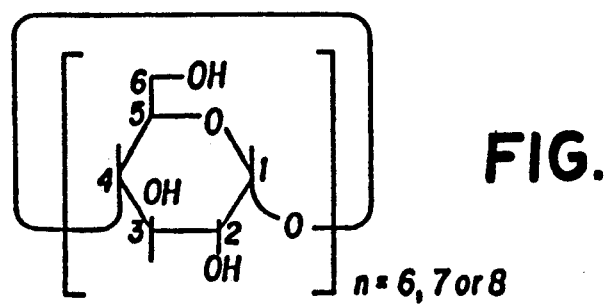

United States Patent [19]

Folkman et al.

[11] Patent Number: 5,019,562
[45] Date of Patent: May 28, 1991

[54] GROWTH INHIBITING AGENT AND THE USE THEREOF

[75] Inventors: Moses J. Folkman, Brookline, Mass.; Paul B. Weisz, Yardley, Pa.

[73] Assignee: The Trustees of the University of Pennsylvania/Childrens Hospital Corporation, Philadelphia, Pa.

[21] Appl. No.: 434,659

[22] Filed: Nov. 9, 1989

Related U.S. Application Data

[63] Continuation of Ser. No. 295,638, Jan. 10, 1989, abandoned, which is a continuation-in-part of Ser. No. 145,407, Jan. 19, 1988, abandoned.

[51] Int. Cl.$^5$ .................... A61K 31/70; C08B 37/02; C08B 37/16
[52] U.S. Cl. ...................................... 514/58; 514/908; 536/103
[58] Field of Search ............ 514/58, 908; 536/103

[56] References Cited

U.S. PATENT DOCUMENTS

| | | | |
|---|---|---|---|
| 4,020,160 | 4/1977 | Bernstein et al. | 514/58 |
| 4,066,829 | 1/1978 | Nair et al. | 536/103 |
| 4,247,535 | 1/1981 | Lewis et al. | 536/103 |
| 4,258,180 | 3/1981 | Lewis et al. | 536/112 |
| 4,383,992 | 5/1983 | Lipari | 514/174 |
| 4,596,795 | 6/1986 | Pitha | 536/103 |
| 4,632,828 | 12/1986 | Carli | 514/178 |
| 4,727,064 | 2/1988 | Pitha | 514/58 |
| 4,757,056 | 7/1988 | Van Gorp | 514/54 |
| 4,783,446 | 11/1988 | Neushul | 514/54 |
| 4,834,985 | 5/1989 | Elger et al. | 424/488 |
| 4,877,774 | 10/1989 | Pitha et al. | 514/26 |
| 4,877,778 | 10/1989 | Carpenter et al. | 514/58 |

FOREIGN PATENT DOCUMENTS 0188821 7/1986 European Pat. Off. .
WO85/02767 7/1985 World Int. Prop. O. .

OTHER PUBLICATIONS

Pitha et al, J. Pharma. Sciences 75: 165–167 (Feb. 1986).
Mitsui Pharm. Inc., Japan 60-11475, Jan. 21, 1985.
Asano, Japan 53-109953, Sep. 26, 1978.
Chemical Abstracts, vol. 83, No. 9., 9/1/75 Abstract 83:795 44a.

Primary Examiner—Ronald W. Griffin
Attorney, Agent, or Firm—Pennie & Edmonds

[57] ABSTRACT

Pathological or otherwise undesirable cell or tissue growth in mammals, including humans, is inhibited by administering thereto a composition exemplified by (1) a water-soluble cyclodextrin sulfate salt, together with (2) a growth-inhibiting organic compound. The growth-inhibiting compound (2) may be a steroid having no inhibiting effect in the absence of (1), or an organic compound which may be an active growth inhibitor, the action of which is potentiated by (1). The invention provides a method for inhibiting angiogenesis and controlling the growth of tumors as well as treating other diseases and pathological conditions associated with undesired cell or tissue growth, including angiogenesis.

24 Claims, 5 Drawing Sheets

GROWTH INHIBITING AGENT AND THE USE THEREOF

CROSS REFERENCE TO RELATED APPLICATION

This application is a continuation of application Ser. No. 07/295,638 filed Jan. 10, 1989 now abandoned, which in turn is a continuation-in-part of application Ser. No. 145,407 filed Jan. 19, 1988, now abandoned.

TABLE OF CONTENTS

1. Field of the Invention
2. Background of the Invention
   2.1. Heparin and Inhibition of Angiogenesis
   2.2. Cyclodextrins
3. Advantages and Objects of the Invention
4. Summary of the Invention
5. Brief Description of the Figures
6. Detailed Description of the Invention
   6.1. Water-Soluble Derivatives of Cyclodextrins
   6.2. Steroids and Non-Steroidal Organic Compounds
   6.3. Applications and Methods of Use
7. Examples

1 FIELD OF THE INVENTION

This invention is concerned broadly with the inhibition of pathological or undesired cell or tissue growth in mammals by use of a new growth-inhibiting composition. More specifically, the present invention is directed to a growth-inhibiting composition comprising a highly soluble cyclodextrin derivative and a latent or active growth-inhibiting compound, and to the use of this composition to inhibit undesired or pathological growth, including angiogenesis which is associated with, inter alia, the growth of malignant tumors.

2. BACKGROUND OF THE INVENTION

2.1. Heparin and Inhibition of Angiogenesis

Angiogenesis, the induction of growth of new capillary blood vessels, is important in normal processes such as development of the embryo, formation of the corpus luteum and healing of wounds. It is also an important component in pathological processes such as chronic inflammation, certain immune responses, and neoplasia. It is now accepted that angiogenesis is induced by most malignant tumors and that it is necessary for their continued growth and survival. It is also recognized that angiogenesis is a major component of a number of ophthamological pathologies including such as diabetic retinopathy, retrolental fibroplasia and neovascular glaucoma. Additionally, angiogenesis is now recognized as a major component in other non-neoplastic pathological conditions including rheumatoid arthritis, in which abnormal capillary growth can destroy joint cartilage; hemanogiomas, in which abnormal capillary proliferation appears in newborns and can persist for up to 2 years; angiofibromas which develop in the nasopharynx; and psoriasis, in which excessive proliferation and shedding may be dependent on abnormal capillary growth in the dermis [see Folkman and Klagsbrun, Science 235:442 (1987)].

It has been previously discovered that heparin (or heparin fragments) and cortisone will co-act together to inhibit angiogenesis. This is described in U.S. Pat. application Ser. No. 641,305 filed Aug. 16, 1984, the contents of which are incorporated herein by reference. When administered together to mice with certain kinds of tumors, this combination can inhibit the generation of essential capillary vessels that support tumor growth, and can cause the collapse of the blood supply which supports the tumors. A review of the history of this discovery and of related subject matter is contained in the publication "How is Blood Vessel Growth Regulated in Normal and Neoplastic Tissue?" (G H.A. Clowes Memorial Award Lecture), Judah Folkman, Cancer Research, 46:467 (1986) the contents of which are incorporated herein by reference for background.

Cortisone is an anti-inflammatory agent that by itself does not have the ability to inhibit capillary growth. It has been reported in Shubik et al., J. Nat'l Cancer Inst. 57:769 (1976) that 6 α-methyl prednisolone partially suppressed tumor angiogenesis in hamster cheek pouches under certain conditions, but tumor growth was not stopped. Many other publications have reported continued growth of tumors even in the presence of large amounts of cortisone. It has also been reported [Gross et al., Proc. Nat'l. Acad. Sci. USA 78:176 (1981)] that medroxyprogestrone, dexamethasone and to a lesser extent cortisone, inhibited tumor angiogenesis in rabbit corneas, while estradiol and testosterone were ineffective.

Aside from cortisone, certain other steroids are now known to successfully suppress angiogenesis when administered together with heparin or certain heparin fragments. The effective steroids have been referred to as "hepar-independent" because heparin was (until now) unique in its effect. The findings and the character of desirable angiostatic steroids has been discussed in "A New Class of Steroids Inhibits Angiogenesis in the Presence of Heparin or a Heparin Fragment", R. Crum, S. Szabo and J. Folkman, Science 230:1375 (1985); and in "Angiostatic Steroids", J. Folkman and D.E. Ingber, Annals of Surgery, 206:374 (1987) incorporated herein by reference for background purposes.

Heparin, a mucopolysaccharide, is a constituent of various tissues, especially liver and lung, and mast cells in several mammalian species. Chemically, it has been described as an α, βglycosidically linked sulfated copolymer of D-glucosamine and D-glucuronic acid. However, although heparin has been used clinically as an anti-coagulant for half a century, both the exact structure of the precise nature by which it acts in blood anti-coagulation have not been discovered. Much of the difficulty in determining the structure of heparin results from its complexity and the fact that it is not a homogeneous, well-defined substance. Heparin is polydisperse with a molecular weight range from about 5,000 to 40,000. Within a given chain, there are also structural variations such as the varying degrees of sulfation, N-acetylation and C-5 epimerization in the uronic acid residue.

A major disadvantage in the use of heparin with a steroid to inhibit angiogenesis results from the fact that heparins manufactured by different processes and different companies revealed quite different antiangiogenic activities despite similar anticoagulant activities. The precise composition of commercial heparin apparently varies depending on its source and method of manufacture. While some heparins may be combined with cortisone to inhibit angiogenesis, other heparins are not effective as such. In fact, some heparins in order to be effective may be required in such high doses that administration may cause problems due to the anticoagulant activity of heparin. A second disadvantage is that while heparins apparently can inhibit the growth of responsive tumors when administered in the proper dose range and proper ratio to steroid, and even, promote regression at somewhat higher doses and ratios; heparins can also cause resumption of rapid tumor growth when administered at even higher dose levels and ratios to steroid. The apparent presence of both positive and negative regulators of angiogenesis in heparin may create problems in properly administering the drug. An additional disadvantage derives from the anti-coagulant activity of heparin, restricting its use to low dosage levels or to oral administration in order to avoid bleeding. Finally because heparin cannot penetrate the corneal membrane, it cannot be topically applied to the exterior of the cornea for its desired antiangiogenic activity.

2.2. CYCLODEXTRINS

Cyclodextrins (hereinafter referred to for convenience as CD or CDs for the singular and the plural, respectively) are cyclic oligosaccharides consisting of at least six glucopyranose units. Although CDs with up to twelve glucopyranose units are known, only the first three homologs have been studied extensively. These compounds have the simple, well-defined chemical structure shown in FIG. 1(A). The common designations of the lower molecular weight $\alpha$-, $\beta$- and $\gamma$-CDs are used throughout this specification and will refer to the chemical structure shown in FIG. 1(A) wherein $n=6$, 7, or 8 glucopyranose units, respectively. The initial discovery of the CDs as degradation products of starch was made at about the turn of the century, and Schardinger showed that these compounds could be prepared by the action of *Bacillus macerans* amylase upon starch. In older literature, the compounds are often referred to as Schardinger dextrins. They are also sometimes called cycloamyloses.

Figure 1B:
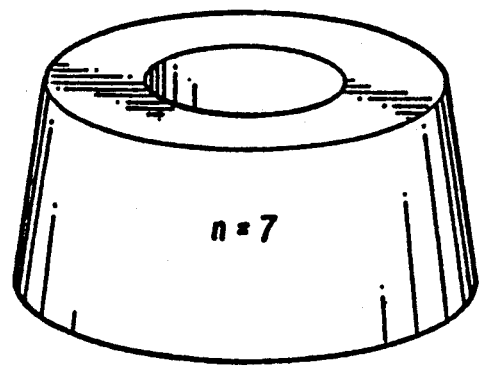

Topographically, the CDs may be represented as a torus, as shown in FIG. 1(B), the upper rim of which is lined with primary —$CH_2OH$ groups, and the lower rim with secondary hydroxyl groups. Coaxially aligned with the torus is a channel-like cavity of about 5, 6 or 7.5 A.U. diameter for the $\alpha$-, $\beta$-, and $\gamma$-CDs, respectively. These cavities make the cyclodextrins capable of forming inclusion compounds with hydrophobic guest molecules of suitable diameters.

A reasonably large number of CD derivatives have been prepared and described in the literature. In general, these chemically modified CDs are formed by reaction of the primary or secondary hydroxyl groups attached to carbons 2, 3 or 6 [FIG. 1(A)], without disturbing the $\alpha$ (1→4) hemiacetal linkages. A review of such preparations is given in "Tetrahedron Report Number 147, Synthesis of Chemically Modified Cyclodextrins", A. P. Croft and R. A. Bartsch, Tetrahedron 39(9):1417–1474 (1983), incorporated herein by reference for background (hereinafter referred to as "Tetrahedron Report No. 147").

In particular, $\alpha$-, $\beta$-, and $\gamma$-CD sulfates (Na salt) are shown as Compound Nos. 207, 208, and 209 in Tetrahedron Report No. 147, (supra) Table 26, p. 1456. U.S. Pat. No. 2,923,704 to Berger describes the preparation of cycloamylose sulfates. U.S. Pat. No. 4,020,160 to Bernstein et al. disclose the use of modified cyclodextran sulfates as complement inhibitors. U.S. Pat. No. 4,383,992 to Lipari describes the preparation of a water-soluble inclusion compound of a steroid and unmodified $\beta$-cyclodextrin. U.S. Pat. No. 4,596,795 to Pitha discloses the administration (by the sublingual or buccal route) of sex hormones, particularly tetosterone, progesterone and estradiol in the form of their inclusion compounds with hydroxypropyl-$\beta$-CD or poly-$\beta$-CD. None of the foregoing references are believed to show or make obvious applicants' invention as described and claimed herein.

3. ADVANTAGES AND OBJECTS OF THE INVENTION

We have now found that certain simple and very water-soluble derivatives of the cyclodextrins when administered together with a latent growth-inhibiting steroid such as cortisone or hydrocortisone or with a non-steroidal growth-inhibiting organic compound effectively inhibit angiogenesis without exhibiting the undesirable properties of heparin.

One of the objects of the present invention is to provide a novel composition including a derivative of a cyclodextrin and a growth-inhibiting compound, which composition is effective for inhibiting cell or tissue growth, especially angiogenesis, or for treating tumors, in mammals, including humans.

Another object of the invention is to provide pharmaceutical preparations containing a highly water soluble cyclodextrin derivative, especially a cyclodextrin sulfate salt, and one or more steroid compounds.

Another object of the present invention is to provide a method of treating diseases or conditions associated or characterized by angiogenesis by inhibiting undesired angiogenesis in mammals, including humans, in need of such treatment.

A further object of the present invention is to provide a method for treating mammals, including humans, having a tumor burden, to arrest and/or to regress growth of the tumor masses.

These and other objects, aspects and advantages of the present invention will become apparent to those skilled in the art upon reviewing the following description and appended claims.

4. SUMMARY OF THE INVENTION

This invention provides a composition for inhibiting undesired or pathological cell or tissue growth (including angiogenesis) in mammals, including humans, said composition comprising active agents consisting essentially of (1) a very water-soluble derivative of $\alpha$-, $\beta$- or $\gamma$-cyclodextrin in combination with (2) a latent growth-inhibiting steroid or a non-steroidal growth-inhibiting organic compound.

This invention further provides a method of inhibiting undesired or pathological cell or tissue growth (including angiogenesis) in mammals, including humans, comprising administering thereto a growth-inhibiting amount of active agents consisting essentially of (1) a very water-soluble derivative of $\alpha$-, $\beta$- or $\gamma$-cyclodextrin in combination with (2) a latent growth-inhibiting steroid or a non-steroidal growth-inhibiting organic compound. This method of the invention can be accomplished either by mixing the two active agents and administering the combination via a single route or, alternatively, by administering each of the active agents separately and permitting the combination to form in vivo. According to the alternative mode, the two active agents can be administered separately via the same or different routes, so long as both agents are thus allowed to be present simultaneously in combination in vivo.

This invention further provides a method of inhibiting angiogenesis in mammals, including humans, comprising administering thereto an angiogenesis-inhibiting amount of a composition comprising active agents consisting essentially of (1) a very water-soluble derivative of α-, β- or γ-cyclodextrin in combination with (2) at least one angiogenesis inhibitor selected from the group consisting of a latent growth-inhibiting steroid and a non-steroidal growth-inhibiting organic compound, said derivative being characterized by a solubility in distilled water of at least about 20 grams per 100 milliliters of water at 0° C.

This invention further provides a method of inhibiting the pathological growth of smooth muscle cells in mammals, including humans, in need of such treatment, which method comprises administering thereto a growth-inhibiting amount of a composition comprising as active agent a very water-soluble cyclodextrin derivative; preferably a very water-soluble cyclodextrin sulfate salt consisting essentially of the sulfated anion of α-, β- or γ-cyclodextrin associated with a non-toxic physiologically acceptable cation.

5 BRIEF DESCRIPTION OF THE FIGURES

The present invention may be more fully understood by reference to the following detailed description of the invention, examples of specific embodiments of the invention and appended figures in which:

FIG. 1(A and B) is a schematic representation of: (A) the chemical structure of α-, β- and γ-cyclodextrins; and (B) of the three-dimensional shape of these cyclodextrins.

Figure 2A:
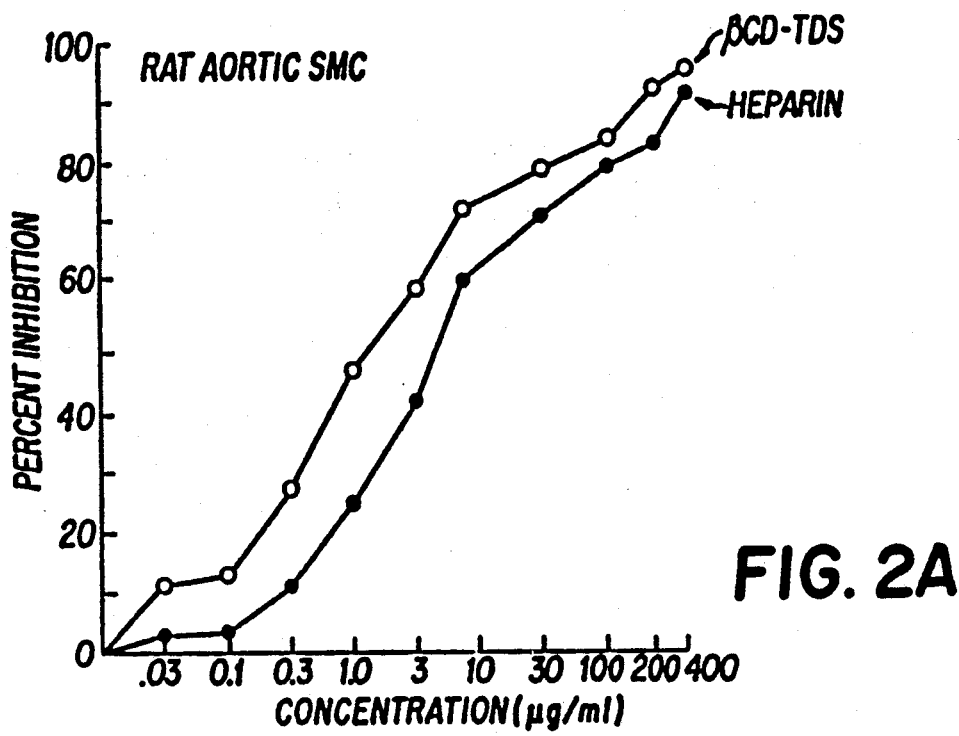
Figure 2B:
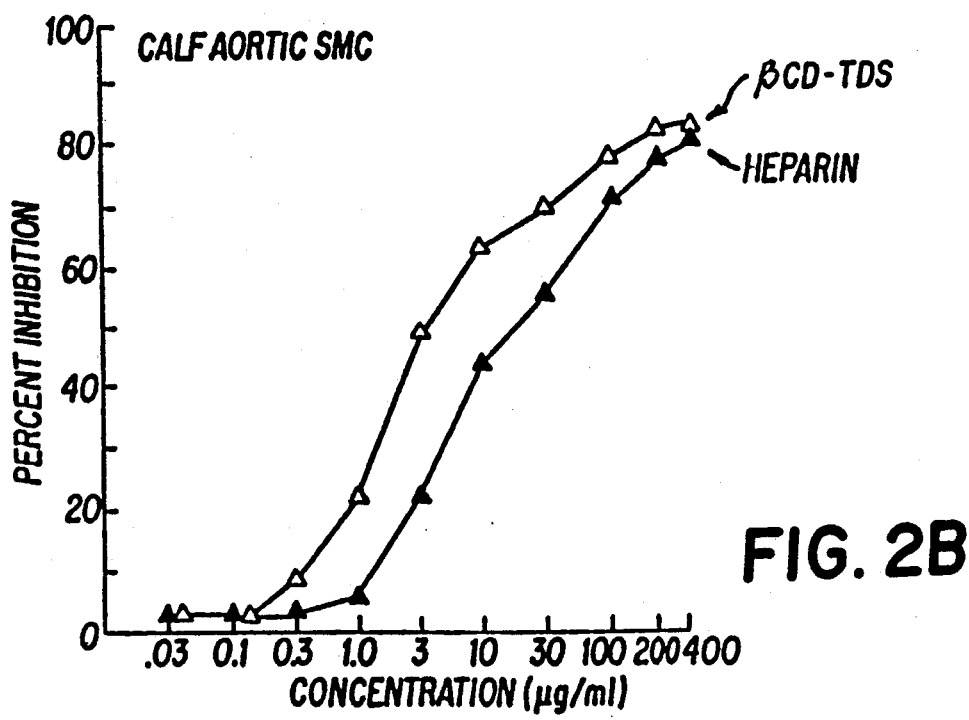

FIG. 2 (A and B) graphically illustrates the effect of β-cyclodextrin tetradeca sulfate (β-CD-TDS) or heparin on growth of (A) rat aortic smooth muscle cells and (B) calf aortic smooth muscle cells in tissue culture.

FIG. 3(A-D) is a photographic representation of the effect of topically administered agents on endotoxin-induced capillary vessel development in the rabbit cornea. Effects of (A) Endotoxin alone (i.e., Control Group); (B) hydrocortisone alone, (Group 2); (c) β-CD-TDS+hydrocortisone, (Group 3); and (D) β-CD-TDS alone (Group 4) are shown. See text for experimental details.

Figure 4:
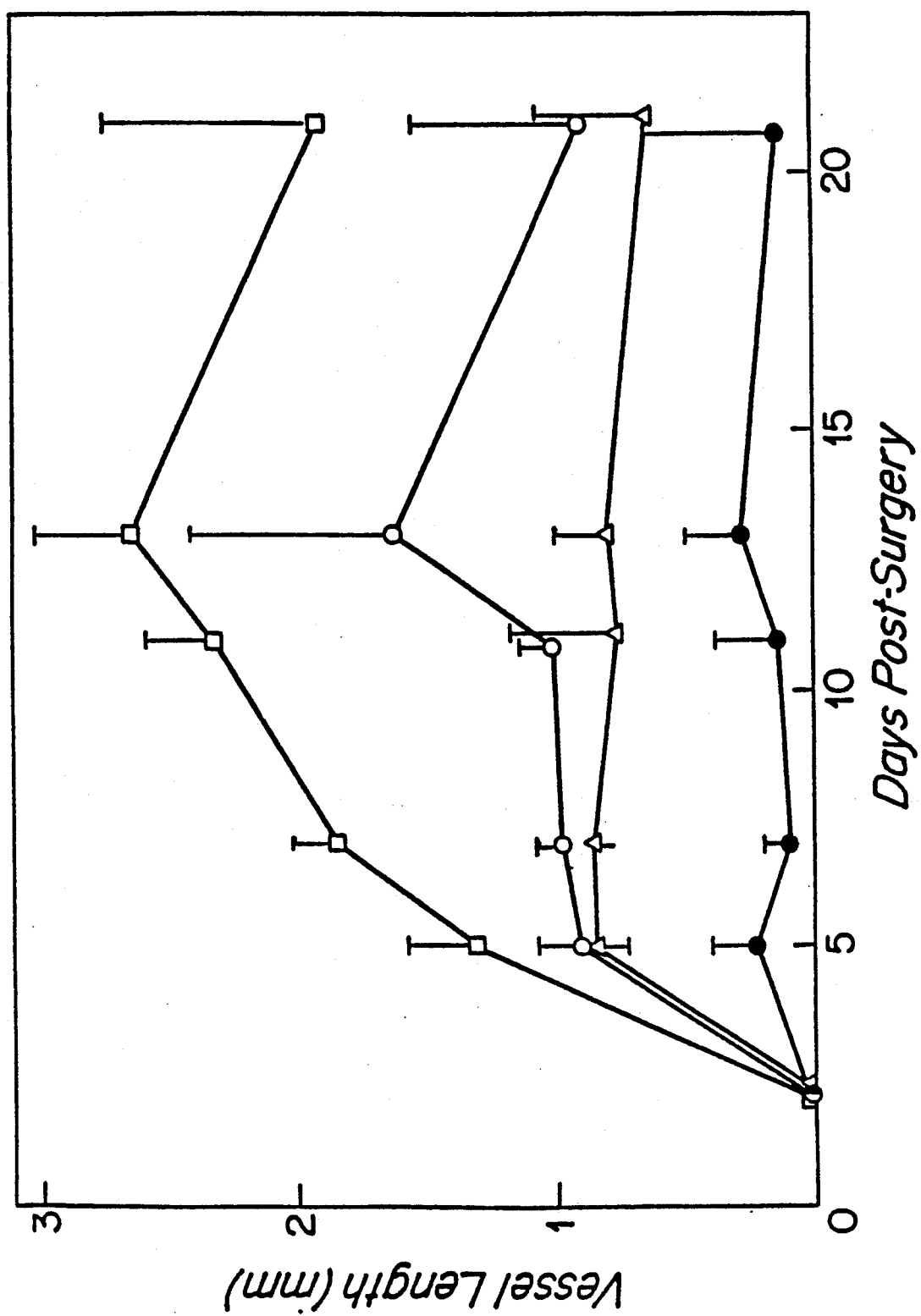

FIG. 4 graphically illustrates the effect of implantation of sustained release polymers incorporating various agents on endotoxin-induced capillary blood vessel elongation in the rabbit cornea. [○]=Endotoxin alone, (Control Group); [●]=β-CD-TDS+Cortexolone, (Group 2); [△]=Cortexolone alone, (Group 3); and [□]=β-CD-TDS alone, (Group 4). See text for experimental details.

6. DETAILED DESCRIPTION OF THE INVENTION

The present inventors searched for a compound other than heparin, which would not have the disadvantages of heparin, but which when combined with a steroid would be effective for suppressing undesired or pathological cell or tissue growth including angiogenesis and, therefore, would be effective, inter alia, for controlling or eliminating tumors in mammals, including humans.

Because of the known ability of cyclodextrins including β-CD to form water soluble inclusion compounds with steroids, we attempted to make use of mixtures of unmodified CDs with hydrocortisone. However, it was discovered that such mixtures had no effect for suppressing angiogenesis, as shown by Examples 18-20 (infra, Section 7).

Quite surprisingly, we discovered that highly water-soluble salts of cyclodextrin in combination with a steroid, such as hydrocortisone, were effective for inhibiting angiogenesis. In particular, β-CD tetradeca sulfate (β-CD-TDS) was found to be very effective. In other words, a composition comprising a steroid and a water-soluble cyclodextrin derivative is effective for inhibiting undesired cell or tissue growth, including angiogenesis, and for treating tumors in mammals.

The CD sulfates and other highly water-soluble derivatives discussed herein have been found to be reproducible in their effect in the chick chorioallantoic membrane (CAM) assay described below. This assay has been employed as a model assay to detect angiogenic activity of various substances. [Klagsbrun et al., Cancer Res. 36:10(1976)]. Three separate batches of β-CD-TDS prepared by the method described in Example 1(A) were compared in the CAM assay. Results for the three separate batches were indistinguishable. The highly water-soluble CD derivatives mimic the advantageous features of antiangiogenic heparin without its disadvantages. These findings also set aside the notion that heparin is unique in its role in suppressing angiogenesis when combined with a suitable steroid.

We have also found that use of a highly water-soluble CD derivative such as β-CD-TDS together with a non-steroidal compound that inhibits growth in the absence of exogenous heparin, i.e., a compound that inherently has some antiangiogenic activity, surprisingly potentiates the antiangiogenic activity of such compound. Examples of such non-steroidal compounds include, but are not limited to proline analogs such as L-2-azetidinecarboxylic acid,

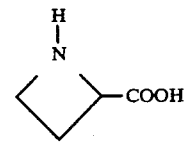

(see, infra, Example 24), cishydroxyproline, or 3,4-dehydroproline, and transretinoic acid, and fumagillin, a compound produced by a strain of Aspergillus (see, infra, Example 24). L-2-azetidinecarboxylic acid is described in Merck under Compound 911, which description is incorporated herein by reference. Fumagillin is a known compound having the empirical formula $C_{26}H_{34}O_7$ (mol. wt.=458.3), and its structure and method of preparation are described in Merck under Compound No. 8591, which entire description is incorporated herein by reference. [See Ingber and Folkman Lab. Investig. 59:44 (1988) for a description of such non-steroidal growth inhibiting compounds which are proline analogs.] The use of either L-2-azetidinecarboxylic acid or fumagillin, each alone, or with heparin or a heparin fragment, are not part of the present invention.

To clearly distinguish the steroids (which in the absence of exogenous heparin, have no inherent antiangiogenic activity) from such non-steroidal growth-inhibitory compounds, the qualifying phrase "latent growth-inhibiting" is used herein. The adjective "non-steroidal" as used herein means a compound in which carbon ring structure characteristic of a steroid is absent.

6.1. WATER-SOLUBLE DERIVATIVES OF CYCLODEXTRINS

Highly water-soluble CD derivatives bearing non-ionic and/or ionic substituents are useful for inhibiting undesired growth according to the present invention. Suitable highly water-soluble CD derivatives include $\alpha$, $\beta$ and $\gamma$ CD derivatives having non-ionic substituents including but not limited to alkyl substituents such as methyl, ethyl, etc., as well as those in which a number of hydroxyl groups are replaced by other groups so as to increase the hydrophilic activity of the CD. Such groups may include, esters, ethers, thioesters, thioethers, carboxylic acids or other groups which convey hydrophilic activity by way of polar or hydrogen bonding constituents or they may include partial hydroxyl substitution that allows better hydrogen bonding involving the remaining hydroxyl groups.

The CD derivatives useful in the present invention are highly hydrophilic and therefore very water soluble. Without wishing to be bound by theory, we believe that a highly hydrophilic character is important to allow interaction with cellular surfaces. We also believe a very high water solubility of the derivative is an important factor which cooperatively interacts with the inherent complexing ability of the CD structure to provide effective inhibition of angiogenesis with an exogenous steroid, as provided by this invention. We believe that the hydrophlilic activity is roughly indicated by the affinity to water, as measured by water solubility. It is important to measure the same at 0° C. since at higher temperatures the most suitable derivative have solubilities so high that meaniningful measurements are difficult.

As shown in Table III (Examples 18-22, infra, Section 7), the most soluble derivatives (measured at 0° C.) show the highest antiangiogenic activity. Of the CDs, the $\beta$-CD derivatives appear to be most effective. In genera, useful potency is evident at a solubility, measured at 0° C., of at least about 15 gm/100 ml in distilled water, preferably at least about 20 gm/100 ml, more preferably about 30 gm/100 ml. All solubility measurements referred to herein relate to the solubility of the substantially anhydrous derivatives, and when these are salts, to the anhydrous sodium form. The term "very soluble" as used herein refers to a solubility of at least 15 gm/100 ml measured as described above.

It is contemplated that very water-soluble CD derivatives bearing ionic and/or non-ionic substituents may in some instances have advantageous properties, and that these are within the scope of this invention. Although highly water-soluble derivatives in general are believed useful, salt derivatives are preferred.

The phrase "salt derivative" as used herein means an ionic compound derived from a CD by reaction with a suitable reagent. The preferred salt derivatives are provided by a cyclodextrin having substituents selected from the group consisting of sulfate, phosphate, carboxylate and mixtures thereof associated with a non-toxic, physiologically acceptable cation. Many of said preferred derivatives are known compounds. (See, Tetrahedron Report Number 147, supra). But many potentially useful forms may be variants, structurally or chemically of known compounds. They also may possess several different substituents such as is the case of the cyclodextrin propoxyl sulfate of Example 1D, which we believe has not previously been reported. Some of the preferred salt forms of the derivatives are the sodium and potassium forms, since these tend to impart increased water solubility to organic anions. The salt derivatives useful herein will exhibit electrolytic conductivity and osmotic properties characteristic of electrolytes and polyelectrolytes when in aqueous solution. A particularly preferred salt derivative is $\beta$-cyclodextrin tetradeca sulfate ($\beta$-CD-TDS).

The $\alpha$-, $\beta$- and $\gamma$-CD sulfate salts are all usable in the presently claimed invention. $\beta$-CD sulfate salts are preferred. Various degrees of sulfation per glucose unit can be employed, such as average of one sulfate group per two glucose units of two sulfate groups per glucose unit. Cyclodextrins having about two sulfate groups per glucose unit are preferred. Especially preferred is $\beta$-CD-TDS which has an average of two sulfate groups per glucose unit.

6.2. STEROIDS AND NON-STEROIDAL ORGANIC COMPOUNDS

Among the steroids which are effective and can be utilized in the presently claimed invention are the following:

17 alpha, 21-dihydroxy-4-pregene -3,11,20-trione and its 21acetate (or cortisone);

11 alpha, 17,21-trihydroxypregn-4-ene-3,20-dione (or 11 alpha hydrocortisone);

11 beta, 17 alpha, 21-trihydroxypregn-4-ene-3,20-dione (or hydrocortosone);

17 alpha, 21-dihydroxypregna-4,9(11)-diene-3,20-dione;

15 alpha, 17 alpha, 21-trihydroxy-4-pregnene-3,20-dione;

16 alpha, 17 alpha, 21-trihydroxy-6 alpha-methylpregn-4-ene-3, 20-dione-21-acetate-16,17 cyclic ketal of acetone;

6 alpha-fluoro-17 alpha, 21-dihydroxy-16 beta-methyl-preqna-4, 9(11)-dinene-3,20-dione;

6 alpha-fluoro-18 alpha,21-dihydroxy-16 beta-methyl-pregna-4, 9(11)-diene-3,20-dione-17,21-diacetate;

6 beta, 17 alpha, 21-trihydroxypregn-4-ene-3,20-dione;

17 alpha, 21-dihydroxypregn-4-ene-3,20-dione-21-acetate;

17 alpha, 21-dihydroxypregn-4-ene-3,20-dione (or Cortexolone);

9 beta, 11 beta-epoxy-17 alpha, 21-dihydroxy-2 alpha-methylpregn-4-ene-3, 20-dione-21-acetate;

17 alpha, 21-dihydroxy-16 alpha-methylpregn-4-ene-3,20-dione;

9 alpha, 11 beta-dichloro-17 alpha, 21-dihydroxypregn-4-ene-3, 20-dione-21-acetate 17 alpha, 21-dihydroxy-6 alpha, 16 alpha-dimethylpregn-4-ene-3, 20-dione-21-acetate;

17 alpha, 21-dihydroxy-16 alpha-methylpregna-4,9(11)-diene-3, 20-dione-21-acetate;

17 alpha, 21-dihydroxy-16 beta-methylpregna-4,9, (11)-diene-3, 20-dione-21-benzoate:

6 alpha-fluoro-17 alpha, 21-dihydroxy-16 beta-methylpregna-4, 9(11)-diene-3,20-dione-17-acetate-21-benzoate;

17 alpha, 21-dihydroxy-16 beta-methylpregna-1,4,9(11)-triene-3, 20-dione-17-succinate sodium monohydrate;

9 alpha-fluoro-11beta, 16 alpha, 17 alpha, 21-tetrahydroxy-pregn-4-ene-3, 20-dione-16, 21-diacetate;

17 alpha, 21-dihydroxy-16 alpha-methylpregna-1,4,9(11)-triene-3, 20-dione-21-succinate sodium monohydrate;

6 alpha-fluoro-17 alpha, 21-dihydroxy-16 beta-methylpregna-1, 4,9 (11)-triene-3,20-dione-21-succinate sodium;

desoxycorticosterone;
testosterone;
estrone; and
tetrahydro S.

More preferred are those steroids which lack glucocorticoid and mineralo-corticoid activity, since such activity is an undesired effect and limits the dose size or extent of use of the steroid for the purpose of the present invention. Among such more preferred steroids are 11 alpha, 17,21-trihydroxypregn-4-ene-3,20-dione (or 11 alpha-hydrocortisone), 17 alpha, 21-dihydroxypregn-4-ene-3,20-dione (11-desoxycortisol or Cortexolone), and 17 alpha, 21-dihydroxypregna-4, 9(11)-diene-3,20-dione.

None of the steroids themselves effectively inhibits angiogenesis nor causes regression of tumors in the absence of a water-soluble cyclodextrin derivative of the present invention.

As taught by the present invention, the growth-inhibitory activity of non-steroidal organic compounds is potentiated by combination with a water-soluble cyclodextrin derivative. Among the non-steroidal growth-inhibiting organic compounds which are effective and can be utilized in the presently claimed invention are the following: proline analogs such as L-2 azetidinecarboxylic, cishydroxyproline, and 3,4-dehydroproline and transretinoic acid acid, and fumagillin.

Additionally, any non-steroidal organic compound which in combination with a cyclodextrin derivative demonstrates growth inhibiting activity in either of the bioassays described below can be utilized in the methods of the presently claimed invention.

Several bioassays have been developed to estimate the angiogenic-inhibiting potency, if any, of a substance. The rabbit cornea is the basis of one of these methods. The cornea is avascular. A small pocket can be made in it and a tumor implant can be inserted while the rabbit is anesthetized. The tumor is separated from the vascular bed of the host. New capillary blood vessels will grow in a linear manner toward the tumor, and the rate of vessel growth can be measured. [For a more detailed description of this assay, see, Gimbrone et al., J. Nat'l Cancer Inst. 52:413 (1973) incorporated herein by reference].

A more economic bioassay makes use of the chorioallantoic membrane of the chick embryo. This test will for convenience be referred to hereinafter as the "CAM assay". For a more detailed description of the CAM assay, see Folkman et al., Science 221:719 (1983), incorporated herein by reference. A typical CAM assay, such as used for the evaluations in the examples in Section 7, infra, employs 16 eggs per experiment. A 2 mm diameter disk of methylcellulose containing the test substance is applied to the chorioallantoic membrane of a 6-day chick embryo, cultured in a Petri dish, in a humidified incubator with 3% carbon dioxide. Two days later (8-day embryo), the membrane is examined under a stereomicroscope at six- to ten-fold magnification. Inhibition of angiogenesis by the test substance is evidenced by the development of an avascular zone around the methylcellulose disc. An avascular zone of 4 mm is graded as (++) and an avascular zone of 2 mm is graded at (+). The potency of the inhibition at the 2 mm and 4 mm zone(s) are expressed as the percentage of the total number of eggs (usually 16) in the test that were rated (++) or (+), i.e., the % of "successes". A rating of zero % reflects absence of inhibition of the test substance under the test conditions.

The sustained release methylcellulose discs are prepared by dispersing appropriate amount(s) of the test substance of substances in an 0.45% aqueous solution of methylcellulose, and depositing 10 microliter aliquots of the resulting solution in a Teflon mold, followed by air drying for about one hour in a laminar flow hood.

A very advantageous feature of the CAM assay is the very high sensitivity of the chick embryo to toxic substances. Moreover, the lack of toxicity of a substance in the CAM assay has been correlated with lack of toxicity of such substance when administered to other animals.

6.3. APPLICATIONS AND METHODS OF USE

The composition of the present invention is useful for inhibiting undesired cell and tissue growth, including angiogenesis. Of course, the composition of the present invention comprising a water soluble derivative of an $\alpha$-, $\beta$- or $\gamma$-CD and a steroid is to be administered to mammals including humans in need of such treatment. For example, mammals with tumors are in need of treatment with the composition of the present invention. While not completely understood, it is believed that treatment with the composition of the present invention inhibits the creation of new capillaries necessary for tumor growth. This results in the tumor having an insufficient supply of nutrients essential for its growth or even for its vitality. Thus, tumors in mammals including humans, when treated in accordance with the present invention, do not grow and may even lose their vitality and die. Among the tumors contemplated as responsive to the composition and methods of this invention are Reticulum Cell Sarcoma, Lewis Lung Carcinoma, B-16 Melanoma, and Bladder Carcinoma, etc.

Neither mature non-growing blood vessels nor vascular tissue appear to be affected by the treatment with the composition of the present invention. Inhibition of angiogenesis in accordance with the present invention, in addition to its effect upon tumor regression and metastasis in tumor-bearing animals, may be effective in treating a number of other ailments.

The present invention further provides a method for treatment of a number of other non-tumorous disorders which are characterized by pathological cell or tissue growth, including angiogenesis. Thus the invention provides a method for treatment of mammals, including humans, afflicted with a number of non-neoplastic pathological conditions including rheumatoid arthritis, in which abnormal capillary growth can destroy joint cartilage; hemangiomas, in which abnormal capillary proliferation appears in newborns and can persist for up to 2 years; angiofibromas which develop in the nasopharynx; psoriasis, in which excessive proliferation and shedding may be dependent on abnormal capillary growth in the dermis. Additionally, the present invention provides a method for treatment of a number of ophthalmological pathologies which are associated with undesired angiogenesis, including diabetic retinopathy, retrolental fibroplasia and neovascular glaucoma.

The present invention further provides a method for inhibiting undesired smooth muscle cell development often observed following angioplasty or treatment to remove atherosclerotic plaques which occlude blood vessels.

According to one embodiment of the method of the present invention, the active agents are mixed together prior to administration so that the steroid compound or non-steroidal growth-inhibiting compound is administered in combination with the water-soluble cyclodextrin derivative. After the mixture is prepared, it may be administered orally or parenterally including, inter alia, topical application, intravenous, intra-arterial or subcutaneous injection, and including absorption as well as injection and introduction into body apertures or orifices.

Cortisone and its physiologically accepted non-toxic derivatives, such as the acetates, as well as many other steroids useful in the present invention, are only slightly soluble in water. However, when combined with the water-soluble cyclodextrin derivatives of the invention, the resulting complexes have increased water solubility. Accordingly, the composition of the present invention can easily be administered. The term "cortisone" and "hydrocortisone" and 11-α isomer of hydrocortisone as used in the present specification and claims are intended to include both the steroids themselves and their derivatives and structural variants.

According to an alternate embodiment of the method of the invention, the active agents are each administered separately and the combination of the two agents forms in vivo. In this embodiment, the two active agents can be introduced separately either via the same or different routes of administration, so long as both agents are thus present simultaneously in vivo, permitting a complex mixture of the two active agents to form.

Dosages employed are limited only by the well-known limits of the administration of drugs individually for their usual effects, in the case of cortisone, hydrocortisone, or 11-α isomer. Since the CD derivatives useful herein have no anticoagulant effect and show no toxicity in the CAM test at dosages employed according to the method of the invention (see below), they may be administered percutaneously in dosages at least as large as those acceptable for heparin. Oral dosage may be considerably higher. Simple testing, for example by the procedure of Example 3 in U.S. Pat. application Ser. No. 641,305, filed Aug. 16, 1984, suffices to determine effectiveness and optimum dose. The procedure of Example 3 is incorporated herein by reference.

The dose amount required to bring about arrest of tumor growth or regression of tumors varies depending upon the identity of the tumor, as does the length of time required to bring about arrest or regression of tumors. Tumor size at the beginning of treatment also affects the length of time for complete regression. Because administration of cortisone, with or without β-CD-TDS(Na), for example, may result in pulmonary infection after a number of days, it may be desirable to administer a suitable antibiotic as prophylaxis during treatment in accordance with the present invention. Such antibiotics can be mixed with the water-soluble cyclodextrin derivative and the steroid or non-steroidal growth-inhibiting agents of the invention and administered as a mixture or, alternatively, the antibiotics can be administered alone contemporaneously with the water-soluble cyclodextrins and growth-inhibiting agents of the invention either by the same or a different route of administration.

As shown in Table I, infra Section 7, it appears that a weight ratio greater than about 2:1 or a molar ratio of greater than about 0.4 of water-soluble CD derivative to steroid leads to a decrease of antiangiogenic activity. The preferred molar range and the molar ratio of CD derivative to angiostatic agent (steroidal or non-steroidal) is 0.004 to about 0.7. A more preferred useful range is about 0.04 to about 0.7. The latter range is particularly useful in topical applications, including as eye drops for ophtalamological uses. The amount of angiostat will generally be of the order of 0.1 to 10 mg/ml when admixed with the CD derivative, however, the absolute amount may depend on the mode and frequency of administration The effective compositions of this invention are best administered in a suitable carrier, which must be non-toxic and physiologically acceptable, such as water or normal saline solution. Compositions containing mixtures of the active agents or each of the active agents alone, either dry or in a suitable carrier, can be employed.

7. EXAMPLES

The following examples are provided to illustrate this invention. However, they are not to be construed as limiting the scope of the invention, which scope is determined by this entire specification including the appended claims. All amounts and proportions shown are by weight unless explicitly stated to be otherwise. For the CAM assay, however, % refers to the number of "successes". (See Section 6.3, above).

EXAMPLES 1 (A-D)

This example illustrates the best mode known to us for preparing and purifying cyclodextrin sulfates. The method is not per se considered part of the present invention.

(A) β CD-TDS(Na):

β-cyclodextrin (99% pure dihydrate) was purchased from Chemalog (a division of General Dynamics Corp.), South Plainfield, NJ.

5.0 grams of β-cyclodextrin (4.4 mmoles, i.e., about 92 meq —OH) was dissolved in 250 ml of dimethylformamide (DMF) To this solution was added 15.0 grams of $(CH_3)_3N-SO_3$ (108 mmoles) in a single portion and the reaction mixture was heated to 70° C. After two hours at 70° C., a gummy material began to precipitate. The reaction mixture was maintained at 70° C. with vigorous stirring, and then cooled to room temperature. The DMF layer was then decanted and discarded, and the solid residue was dissolved in 250 ml of water followed by addition of 75 ml of 30% sodium acetate. The mixture was stirred vigorously for 4 hours and then poured into 4000 ml of ethanol. After standing overnight, the mixture was filtered to recover the crystallized solids. The filter cake was washed with ethanol (absolute) followed by diethyl ether. The product was then dried under vacuum over $P_2O_5$. 10.3 grams of white powder was recovered. The product was hygroscopic.

The product was analyzed under conditions such that sorption of water was minimized. Elemental analysis gave the following results: C=18.84, H=2.65, S=17.33 (Calculated for $C_6H_8O_{11}S_2Na_2$; C=19.67, H=2.19, S=17.49). $[\alpha]_D^{22}=75°$ (C=2.63 in 0.5 M NaCl). The analysis corresponds to that expected for an average substitution of two hydroxyl groups for each glucopyranose unit, i.e., 14 hydroxyls per CD molecules. The calculated yield for such β-CD-TDS salt is 10.96 grams, about 6% higher than the observed 10.3 grams.

(B) α- and γ-CD-S (Na salt):

The procedure described above was used for these preparations except that 86 mmoles of $CH_3N-SO_3$ was used with β-CD, and 117 mmoles with the γ-CD.

The sulfated α-CD salt analyzed C=18.76; H=2.60; S=16.22. This corresponds on average to a substitution of about 11.7 hydroxyl units per β-CD molecule.

The sulfated γ-CD salt analyzed C=18.92; H=2.69; S=14.84. This corresponds on average to a substitution of about 14 hydroxyl groups per γ-CD molecule.

(C) β CD-SO₄ (Na salt) (7.1 wt% S):

1.0 gm of β-cyclodextrin was dissolved into 50 ml of DMF. To this solution was added 883 mg of (CH₃N.SO₃ (7.2 equivalents). The solution was held at 75° C. for 12 hours, at which time no precipitate had formed. The reaction mixture was cooled to room temperature. To the solution was added 200 ml of ethanol. The resulting colloidal solution was then poured into 600 ml of diethyl ether. A white solid formed in 2 hours. The solid was collected by filtration and then was dissolved in 30 ml H₂O. This solution was stirred for 2 hours. After stirring, the solution was poured into 900 ml of a 2:1 EtOH-Et₂O solution. Crystals formed over an 8 hour period. The crystals were collected and washed with Et₂O. The product was dried over P₂O₅ under vacuum. 1.18 gm of powder was recovered. (72.4% yield).

Elemental analysis of the product showed C=32.49; H=4.99; and S=7.06. This corresponds on average to a substitution of about 3.5 hydroxyls per β-CD molecule.

(D) β-CD-Propoxylate ~14 SO₄

β-CD-(hydroxy-n-propyl ether) was obtained from American Maize-Products Co. (Hammond, IN) and the procedure described above was used to prepare the sulfate salt, β-CD-(~4Pr~14 SO₄).

EXAMPLES 2-15

In these examples the angiogenesis-inhibiting potency of hydrocortisone with various dosage levels of β-CD-TDS prepared as in Example 1 was evaluated by the CAM assay. The methylcellulose discs all contained 60 μg of the steroid but β-CD-TDS was varied from 100 μg down to 0.05 μg. The results are summarized in Table I. As can be seen from the data, angiogenesis inhibition persists with extremely low levels (0.05 μg) of the CD compound with no evidence of activation of angiogenesis at two thousand-fold higher concentration.

TABLE I

| Example No. | Hydrocortisone μg | Beta-CD-TDS μg | CAM Assay (++) % | CAM Assay (+) % |
|---|---|---|---|---|
| 2 | 60 | 100 | — | 57 |
| 3 | " | 50 | 60 | 100 |
| 4 | " | 50 | 22 | 55 |
| 5 | " | 25 | 10 | 60 |
| 6 | " | 25 | 18 | 55 |
| 7 | " | 10 | 40 | 70 |
| 8 | " | 10 | 6 | 40 |
| 9 | " | 5 | 0 | 50 |
| 10 | " | 1 | 0 | 50 |
| 11 | " | 1 | 0 | 42 |
| 12 | " | 0.5 | 0 | 40 |
| 13 | " | 0.1 | 0 | 45 |
| 14 | " | 0.1 | 0 | 37 |
| 15 | " | 0.05 | 0 | 20 |

In contrast With these results, CAM tests made with 100 μg of α-, β- or γ-cyclodextrine with 50 μg of hydrocortisone all showed total absence of angiogenesis-inhibition [no successes at either the 1 mm zone (+) or the 2 mm zone (++) level].

EXAMPLES 16-17

Examples 16 and 17 illustrate the low, but useful, activity afforded by the sulfated α-CD and γ-CD as shown in Table II. Date for Examples 5 and 6 are included for comparison. All tests were made with 25 μg of the indicated CD sulfate and 50 μg of cortisone.

TABLE II

| Example No. | CD | Sulfur, Wt % | CAM Assay (+) % | CAM Assay (++) % |
|---|---|---|---|---|
| 16 | Alpha | 16.2 | 8 | 0 |
| 17 | Gamma | 18.9 | 15 | 0 |
| 5 | Beta-CD-TDS | 17.3 | 60 | 15 |
| 6 | Beta-CD-TDS | 17.3 | 55 | 18 |

EXAMPLES 18-22

This group of examples shows that the angiogenesis suppression activity requires, aside from the characteristic complexing activity of the CD structure, a high water solubility The CAM assays were made with a dosage of 50 μg to 60 μg of hydrocortisone in 10 μl of 0.45% methylcellulose in water.

In order to make comparisons that included the very water-soluble CD sulfates, the solubilities of which were so high at room temperature that measurement was not practical, all solubility measurements were made in liquid water at zero °C. One can picture this to be a measure of the competition of the hydrophilic bonding with water in relation to the orderly bonding of water to itself. These comparisons are summarized in Table III.

Examples 18, 19 and 20 describe the results for the unsubstituted CDs, which gave no indication of angiogenesis suppression activity in the CAM assay. Example 21 shows the results for a sample of propoxylated β-CD (hydroxy-n-propyl ether) obtained from American Maize-Products Co. (Hammond, IN), reported to have an average of about 4 hydroxypropyl groups per CD molecule Examples 22 shows the results obtained with the less sulfated β-CD product from Example 1(C) above. The results for Examples, 16, 17 and 5, including water solubilities at zero °C., are included to complete the comparison.

TABLE III

| Ex. No. | Compound | Conc. μg/10 μl | CAM Assays No. Examples | CAM Assays % Avascular zones | Solubility, 0° C., gm/100 ml H₂O |
|---|---|---|---|---|---|
| 18 | α-CD | 100 | 37 | 5 ± 0.03 | 6 |
|  |  | 25 | 20 | 0 | 6 |
| 19 | β-CD | 100 | 19 | 0 | 0.7 |
|  |  | 25 | 23 | 0.04 | 0.7 |
| 20 | γ-CD | 100 |  | 0 | * |
| 21 | β-CD-propoxylated (~4 Pr) | 100 | 52 | 29 ± 10.5 | 20 |
|  |  | 25 | 50 | 31 ± 9.7 | 20 |
| 21a | β-CD-14Me (~14 Meth) | 100 | 57 | 22 ± 5.7 | 32+ |
|  |  | 25 | 37 | 20 ± 4.2 | 32+ |
| 22 | β-CD- (~7 SO₄) | 100 | 25 | 20 ± 9.6 | 13 |
|  |  | 25 | 27 | 8 ± 3.1 | 13 |
| 22a | β-CD (~4 propoxylated) (~4 SO₄) | 25 |  | 37 | 39 |
| 16 | α-CD (~12 SO₄) | 100 | 40 | 17 ± 4.7 | 36 |
|  |  | 25 | 25 | 4 ± 2.7 | 36 |
| 17 | γ-CD | 100 | 19 | 32 ± 5.3 | 38 |

TABLE III-continued

CAM Assays

| Ex. No. | Compound | Conc. μg/10 μl | No. Examples | % Avascular zones | Solubility, 0° C., gm/100 ml H₂O |
|---|---|---|---|---|---|
| | (~16 SO₄) | 25 | 20 | 19 ± 1.7 | 38 |
| 5 | β-CD-TDS | 100 | 101 | 55 ± 7.5 | 42 |
| | | 50 | 75 | 75 ± 5.8 | 42 |
| | | 25 | 107 | 58 ± 7.0 | 42 |

*Insufficient material available for solubility determination.

EXAMPLE 23

This example illustrates that Cortexolone with β-CD-TDS is an exceptionally effective antiangiogenic composition. Cortexolone is closely related to cortisone chemically. However, it possesses almost none of the functions of cortisone, except for the antiangiogenic effect in the presence of heparin.

Cortexolone, 50 μl/10 μl alone, gave zero % avascular zones in the CAM assay. Q At the same dosage level, with 25 μg/10 μl of β-CD-TDS, the CAM assay showed 85% avascular zones of which 31% are (++) or greater.

EXAMPLE 24

This example demonstrates that β-CD-TDS will potentiate the antiangiogenic activity of fumagillin, a low molecular weight angiogenesis inhibitor produced by a strain of Aspergillus (*Aspergillus fumigatus fresenius*). The inhibitor falls within the class of antibiotics. The fungal angiogenesis inhibitor, its method of preparation, and its use alone or with heparin to inhibit angiogenesis are considered outside the scope of the present invention and are not to be regarded as part thereof.

Examples 24 (a-g) (Table IV) inclusive demonstrate the inherent angiostatic activity as measured by the CAM assay. Examples 24 (h-j) demonstrate that the inherent activity is potentiated by β-CD-TDS. Heparin also potentiates this angiostatic activity (see footnote).

TABLE IV

Fumagillin CAM ASSAYS

| Fumagillin* μg/10 μl | β-CD-TDS μg/10 μl | Avascular Zones |
|---|---|---|
| (a) 50 | 0 | 57% |
| (b) 40 | 0 | 72 |
| (c) 30 | 0 | 62 |
| (d) 20 | 0 | 75 |
| (e) 10 | 0 | 75 |
| (f) 2.5 | 0 | 40 |
| (g) 1 | 0 | 0 |
| (h) 5 | 25 | 100% (2+) |
| (i) 2.5 | 25 | 57 |
| (j) 1.0 | 25 | 33 |

*10 μg Fumagillin with 50 μg heparin produced 100% avascular zones. No avascular zones were produced by either β-CD-TDS or heparin alone at levels shown.

EXAMPLE 25

This example demonstrates that the angiostatic activity of L-2-azetidinecarboxylic acid, which has some inherent angiostatic activity, is strongly potentiated by the presence of CD-TDS. The results of the CAM assay, in the absence and presence of CD-TDS, are given in Table V, Examples 24(a) and 24(b), respectively.

TABLE V

L-2-AZETIDINE

| | μg/10 μl | μg CD-TDS | % Avascular Zones |
|---|---|---|---|
| (a) L-2-Azetidine | 400 | 0 | 28 |
| (b) L-2-Azetidine | 400 | 25 | 100* |

*50% of these avascular zones were 2+, and 25% were 3+, i.e., the largest avascular zones ever observed, greater than 10 mm.

EXAMPLE 26

This example demonstrates the β-CD-TDS is about three times as effective as whole heparin in suppressing smooth muscle cell (SMC) growth when each is used alone (i.e., without exogenous corticosteroid or other supplementation). The bioassay of this activity was made using tissue cultures of rat aortic SMC and calf aortic SMC, with dosages ranging from 0.03 μg/ml up to 400 μg/ml.

The results are shown graphically in FIG. 2(A) and (B).

EXAMPLE 27

This example demonstrates that topical administration of β-C-TDS in combination with hydrocortisone effectively inhibits neovascularization in the cornea.

The rabbit corneal test described by Perlin, Fed. Proc. 36:101 (1977) modified as described below, was employed to examine the effectiveness of a combination of β-CD-TDS and hydrocortisone. In this corneal test, a sustained release polymer impregnated with bacterial endotoxin was first implanted in rabbit corneas. Endotoxin slowly released from this implant induces angiogenesis in the cornea in a manner analogous to the neovascularization observed in patients rejecting a corneal transplant. Rather than employing a second implant containing the test substance to deliver such test substance as generally used, in the present experiments the test substance was applied topically to the cornea, i.e., in the form of eye drops. Animals having received an endotoxin-containing implant were divided into four groups and were treated by topical application (eye drops) as follows: Group 1, was not treated further and served as the control group; Group 2, received hydrocortisone alone (0.5 mg/ml); Group 3, hydrocortisone-21-phosphate and β-CD-TDS, (0.5 mg/ml and 1.0 mg/ml, respectively); and Group 4, β-CD-TDS (1.0 mg/ml). The diluent for the eye drops was saline in all cases. FIG. 3 (A-D) illustrates the results typically obtained on the 9th day post-implantation and treatment.

Figure 3A:
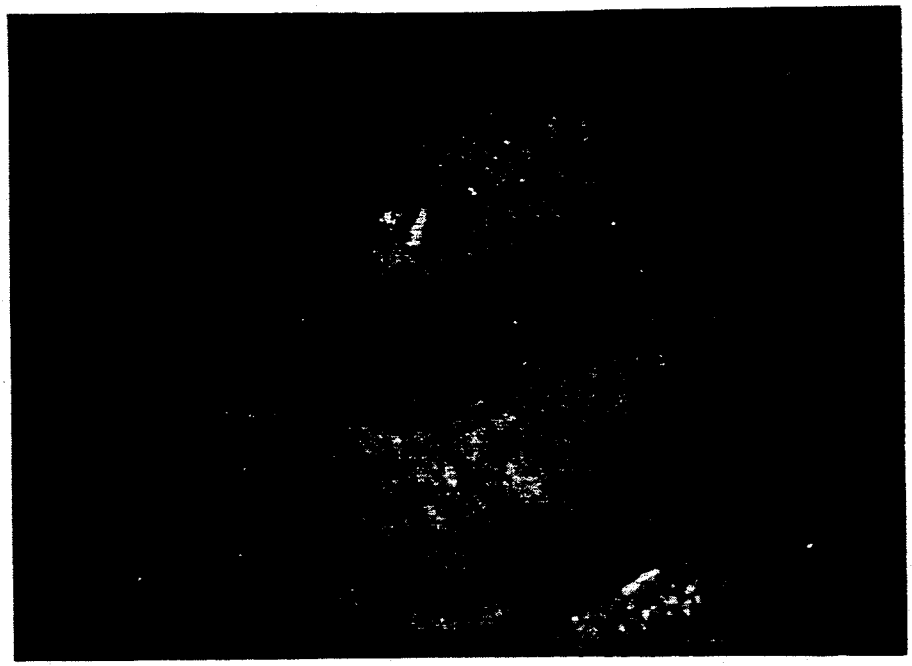
Figure 3B:
Figure 3C:
Figure 3D:
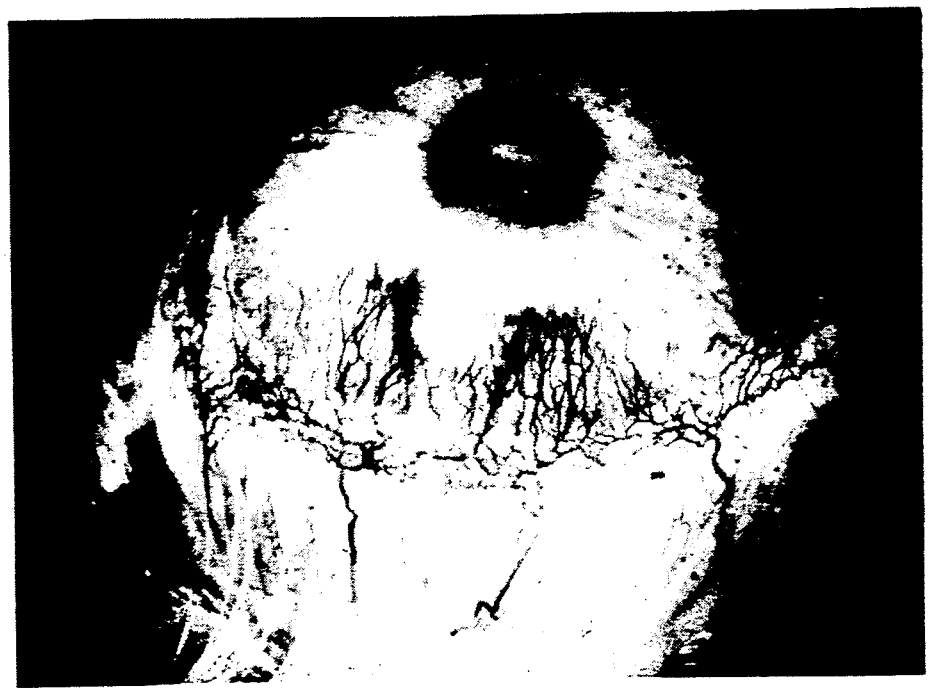

As shown in the photographs of FIG. 3, a combination of hydrocortisone and β-CD-TDS when topically applied to the cornea was very effective in inhibiting angiogenesis (FIG. 3C). The efficacy of this treatment is particularly apparent when the results obtained are compared to those observed in the untreated or control group (FIG. 3C vs FIG. 3A). In fact, in animals treated with hydrocortisone and β-CD-TDS, capillary growth was not only inhibited, but also new capillaries which had formed before initiation of the treatment regressed (FIG. 3C). On the other hand, hydrocortisone alone produced only a slight inhibition of angiogenesis (FIG. 3B). β-CD-TDS alone caused a slight stimulation of angiogenesis (FIG. 3D).

In another series of experiments, the antiangiogenic activity of a water-soluble cyclodextrin salt derivative in combination with cortexolone was evaluated using the rabbit cornea test as described by Gimbrone et al., J. Nat'l Cancer Inst. 52:413 (1974). In these experiments, E. coli endotoxin (17 μg/mm³) incorporated into sustained release polymer pellets of ethylene vinylacetate copolymer [Elvax, Sigma Chemical, St. Louis, MO (hereinafter "Elvax")] was implanted between the vascular limbal edge of the rabbit corneas. The test substance(s) were administered by means of a second Elvax implant incorporating the particular test substance.

Elvax containing endotoxin was implanted into the corneas of 12 rabbits. The animals were then divided into 4 groups and 4 eyes were treated for each group as follows: Group 1, received no further treatment and served as the control group; Group 2, β-CD-TDS at 15 μg/mm³ Elvax pellet; Group 3, cortexolone at 30 μg/mm³ Elvax pellet; and Group 4, a combination of β-CD-TDS and cortexolone incorporated into an Elvax pellat at a final concentration of 15 μg/mm³ Elvax of β-CD-TDS and 30 μg/mm³ Elvax of cortexolone. The vessel length of new capillary growth was measured every 2 days with a slit-lamp stereoscope at 10X using an ocular grid calibrated to +0.1 mm.

Measurement of vessel length alone underestimates the extent of antiangiogenic activity because such measurement does not assess capillary density. Thus, the vessel density was also evaluated and graded using the following scale: 0=no vessels/cornea; 1=1-4 vessels/cornea; 2=5-20 vessels/cornea; 3=20-50 vessels/cornea; and 4=more than 50 vessels/cornea. This grade was then multiplied by mean maximal length of the vessels to obtain a semi-quantitative estimate of vessel density (length-density index) for each cornea. Results obtained are graphically illustrated in FIG. 4 and tabulated in Table VI.

As demonstrated in FIG. 4, the largest difference between treated and control corneas was observed on day 13 after implantation of the Elvax pellets. The mean vessel lengths and vessel density observed on day 13 are listed in Table VI.

TABLE VI

INHIBITION OF ANGIOGENESIS IN CORNEAS

| | Inhibition (% of Untreated Control Group) | | |
| --- | --- | --- | --- |
| | β-CD-TDS Cortexolone | Cortexolone Alone | β-CD-TDS Alone[a] |
| Vessel Length | 18% | 49% | 164% |
| Vessel Density | 8% | 61% | 303% |

[a]Percentage greater than 100% represents stimulation of vessel development.

As shown in Table VI, a combination of β-CD-TDS and cortexolone inhibited linear capillary blood vessel growth to about 18% of that observed in untreated eyes. When capillary density was estimated, this combination suppressed vessel density to about 8% of that observed in untreated eyes. In contrast, as shown in Table VI, when administered alone, cortexolone inhibited linear vessel growth only to about 49% and vessel density to about 61% that observed in untreated eyes. Surprisingly, as further demonstrated in Table VI, administration of β-CD-TDS alone, stimulated vessel growth by about 164% and vessel density by about 303% above that observed in untreated eyes.

Based on these results, it is clear that administration of a cyclodextran salt derivative in combination with a steroid according to the present invention, is an effective method for inhibiting angiogenesis in ophthalmological tissues.

What is claimed is:

1. A composition for inhibiting undesired or pathological cell or tissue growth, including angiogenesis, in mammals, including humans, comprising (1) an ionic derivative of α-, β- or γ-cyclodextrin in combination with (2) a latent growth-inhibiting steroid or a non-steroidal growth-inhibiting organic compound, in which the derivative is characterized by a solubility at 0° C. in distilled water at least about 20 gm/100 ml of water.

2. The composition according to claim 1, in which the derivative of α-, β- or γ-cyclodextrin is an anionic salt derivative of said cyclodextrin having substituents selected from the group consisting of sulfate, phosphate, carboxylate and mixtures thereof associated with a physiologically acceptable cation.

3. The composition according to claim 2, in which the derivative of α-, β- or γ-cyclodextrin is a cyclodextrin sulfate.

4. The composition according to claim 3, in which the cyclodextrin sulfate is α-cyclodextrin tetradeca sulfate.

5. The composition according to claim 1, in which the steroid has 17-alpha and 21-hydroxyl groups, 3- and 20-one groups and in the 16-position hydrogen, hydroxy or a methyl group and non-toxic, physiologically acceptable carboxylates, acetal, ketals and phosphates thereof.

6. The composition according to claim 3, in which the steroid has 17-alpha and 21-hydroxyl groups, 3- and 20-one groups and in the 16-position hydrogen, hydroxy or a methyl group and non-toxic, physiologically acceptable carboxylates, acetal, ketals and phosphates thereof.

7. The composition according to claim 4, in which the steroid has 17-alpha and 21-hydroxyl groups, 3- and 20-one groups and in the 16-position hydrogen, hydroxy or a methyl group and no-toxic, physiologically acceptable carboxylates, acetal, ketals and phosphates thereof.

8. The composition according to claim 7, in which the steroid is cortisone, hydrocortisone or cortexolone.

9. The composition according to claim 1, in which the non-steroidal growth-inhibiting organic compound is L-2-azetidinecarboxylic acid and the derivative of cyclodextrin is a cyclodextrin sulfate.

10. A composition for inhibiting undesired or pathological cell or tissue growth, including angiogenesis, in mammals, including humans, comprising (1) a derivative of α-, β-, or γ-cyclodextrin in combination with (2) a latent growth-inhibiting steroid or a non-steroidal growth-inhibiting organic compound, in which the derivative is characterized by a solubility at 0° C. in distilled water at least about 20 gm/100 ml of water, and in which the molar ratio of cyclodextrin derivative to a latent growth-inhibiting steroid or a non-steroidal growth-inhibiting organic compound is about 0.004 to about 0.7.

11. The composition according to claim 10, in which the steroid has 17-alpha and 21-hydroxyl groups, 3- and 20-one groups and in the 16-position hydrogen, hydroxy or a methyl group and non-toxic, physiologically acceptable carboxylates, acetal, ketals and phosphates thereof.

12. The composition according to claim 11, in which the steroid is cortisone, hydrocortisone or cortexolene.

13. A method for inhibiting undesired or pathological tumor growth, by means of inhibiting angiogenesis associated with a tumor, in mammals, including humans, comprising administering, to a mammal having a tumor, a tumor growth-inhibiting amount of active agents consisting essentially of (1) a derivative of α-, β-, or γ-cyclodextrine in combination with (2) a latent growth-inhibiting steroid or a non-steroidal growth-inhibiting organic compound, the derivative being characterized by a solubility at 0° C. in distilled water of at least about 20 gm/100 ml of water.

14. A method for inhibiting angiogenesis in mammals, including humans, comprising administering to a mammal an angiogenesis-inhibiting amount of active agents consisting essentially of (1) a derivative of α-, β- or γ-cyclodextrine in combination with (2) a latent growth-inhibiting steroid or a non-steroidal growth-inhibiting organic compound, the derivative being characterized by a solubility at 0° C. in distilled water of at least about 20 gm/100 ml of water.

15. The method according to claim 13, in which the derivative of α-, β-, or γ-cyclodextrin is a salt consisting essentially of an anionic derivative of a cyclodextrin having substituents selected from the group consisting of sulfate, phosphate, carboxylate and mixtures thereof associated with a non-toxic physiologically accetable cation.

16. The method according to claim 15 or 12, in which the salt of α-, β- or γ-cyclodextrin is a cyclodextrin sulfate.

17. The method according to claim 13, in which the salt is β-cyclodextrin sulfate.

18. The method according to claim 13 or 14 in which the steroid has 17-alpha and 21-hydroxyl groups, 3- and 20-one groups and in the 16-position hydrogen, hydroxy or a methyl group and non-toxic, physiologically acceptable carboxylates, acetal, ketals and phosphates thereof.

19. The method according to claim 13 or 14 in which the steroid is cortisone, hydrocortisone or cortexolone.

20. The method according to claim 13 or 14, in which the non steroidal growth-inhibiting organic compound is L-2-azetidinecarboxylic acid.

21. A method for inhibiting the pathological growth of smooth muscle cells in mammals, including humans, comprising administering to a mammal, a growth-inhibiting amount of a derivative of α-, β- or γ-cyclodextrine, the derivative being characterized by a solubility at 0° C. in distilled water of at least about 20 gm/100 ml of water.

22. The method according to claim 21, further comprising administering an amount of a latent growth-inhibiting steroid or a non-steroidal growth-inhibiting organic compound, the derivative being characterized by a solubility at 0° C. in distilled water of at least about 20 gm/100 ml of water.

23. The method according to claim 14, in which the derivative of α-, β- or γ-cyclodextrine is a salt consisting essentially of an anionic derivative of a cyclodextrin having substituents selected from the group consisting of sulfate, phosphate, carboxylate and mixtures thereof associated with a non-toxic physiologically acceptable cation.

24. The method according to claim 21, in which the derivative of the α-, β- or γ-cyclodextrin is an ionic derivative.

* * * * *

UNITED STATES PATENT AND TRADEMARK OFFICE
CERTIFICATE OF CORRECTION

PATENT NO. : 5,019,562
DATED : May 28, 1991
INVENTOR(S) : Moses Judah Folkman and Paul B. Weisz It is certified that error appears in the above-identified patent and that said Letters Patent is hereby corrected as shown below:

Insert the following statement at column 1, line 1;

> This invention was made with government support under Grant No. CA45548 awarded by the National Institutes of Health. The government has certain rights in the invention.

Signed and Sealed this

Sixteenth Day of February, 1993

*Attest:*

STEPHEN G. KUNIN

*Attesting Officer*     *Acting Commissioner of Patents and Trademarks*